US010806373B2

(12) United States Patent
Coifman et al.

(10) Patent No.: US 10,806,373 B2
(45) Date of Patent: Oct. 20, 2020

(54) METHOD AND APPARATUS FOR INTELLIGENT FLOW SENSORS

(76) Inventors: Robert E. Coifman, Millville, NJ (US); Charles E. Forbes, Sarasota, FL (US)

(*) Notice: Subject to any disclaimer, the term of this patent is extended or adjusted under 35 U.S.C. 154(b) by 0 days.

(21) Appl. No.: 13/261,309

(22) PCT Filed: Dec. 3, 2010

(86) PCT No.: PCT/IB2010/055559
§ 371 (c)(1),
(2), (4) Date: Jun. 25, 2012

(87) PCT Pub. No.: WO2011/067734
PCT Pub. Date: Jun. 9, 2011

(65) Prior Publication Data
US 2012/0277615 A1    Nov. 1, 2012

Related U.S. Application Data

(63) Continuation-in-part of application No. 12/885,391, filed on Sep. 17, 2010, now abandoned.
(Continued)

(51) Int. Cl.
*A61B 5/087*     (2006.01)
*A61B 7/00*      (2006.01)
*G01F 1/28*      (2006.01)

(52) U.S. Cl.
CPC ............ *A61B 5/0876* (2013.01); *A61B 7/003* (2013.01); *G01F 1/28* (2013.01)

(58) Field of Classification Search
USPC ........ 600/538, 539; 73/23.3, 861.77, 861.78, 73/1.16, 861, 861.351, 861.352, 861.353;
(Continued)

(56) References Cited

U.S. PATENT DOCUMENTS 4,890,480 A * 1/1990 Young .......................... 73/32 A
6,168,568 B1 * 1/2001 Gavriely ...................... 600/529
(Continued)

FOREIGN PATENT DOCUMENTS

WO    WO 9705824 A1 *  2/1997

*Primary Examiner* — Etsub D Berhanu
(74) *Attorney, Agent, or Firm* — Brian K. Johnson, Esq., LLC

(57) ABSTRACT

A single sensor capable of detecting both airflow in spirometry and the full range of sound frequencies needed to track clinically relevant breath sounds is provided. The airflow sensor includes a movable flap with one or more integrated strain gauges for measuring displacement and vibration. The airflow sensor is inherently bidirectional. The sensor is an elastic flap airflow sensor that is capable of detecting data needed for both spirometry and auscultation measurements. The sensor is sterilizable and designed for the measurement of human respiratory airflow. The sterilizable sensor is also suitable for non-medical fluid flow metering applications. Additional devices such as sensors for the ambient level of various chemicals, sensors for temperature, sensors for humidity and microphones, may be affixed to the flap. When the strain gauge is placed in a conventional Wheatstone bridge configuration, the sensor can provide the airflow measurements needed for medical spirometry.

19 Claims, 15 Drawing Sheets

Related U.S. Application Data

(60) Provisional application No. 61/283,402, filed on Dec. 3, 2009, provisional application No. 61/338,468, filed on Feb. 20, 2010, provisional application No. 61/343,053, filed on Apr. 23, 2010, provisional application No. 61/277,289, filed on Sep. 23, 2009.

(58) Field of Classification Search
USPC .................................... 128/204.23, 204.26
See application file for complete search history.

(56) References Cited

U.S. PATENT DOCUMENTS

| | | | |
|---|---|---|---|
| 6,447,459 B1* | 9/2002 | Larom | 600/538 |
| 2004/0255682 A1* | 12/2004 | Petrova et al. | 73/715 |
| 2005/0125169 A1* | 6/2005 | Loose | 702/45 |
| 2007/0044572 A1* | 3/2007 | Davis et al. | 73/861.42 |
| 2007/0277592 A1* | 12/2007 | Johansson et al. | 73/38 |

* cited by examiner

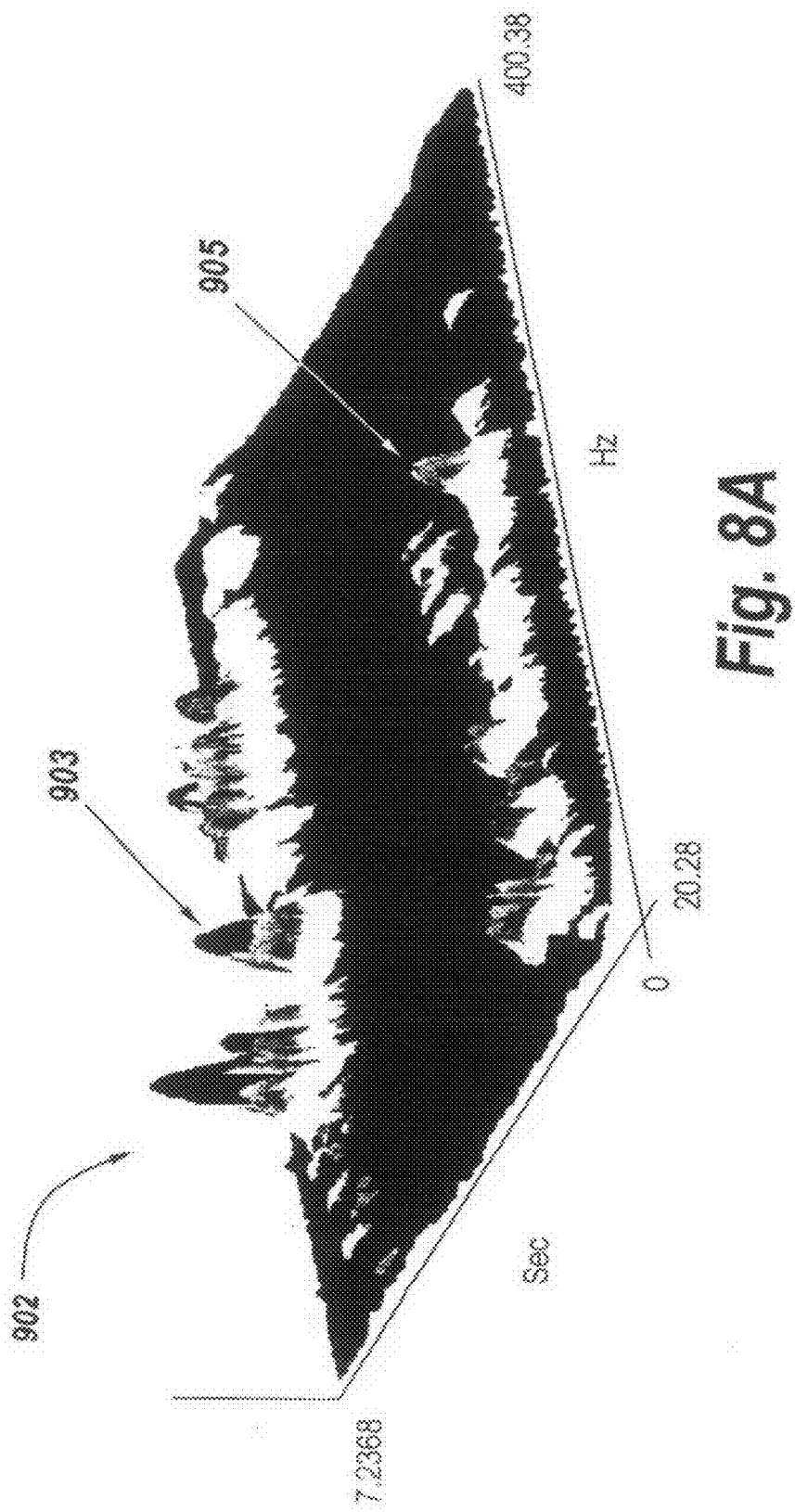

METHOD AND APPARATUS FOR INTELLIGENT FLOW SENSORS

RELATED APPLICATIONS

This application is a 371 of PCT/IB/2010/05559, filed Dec. 3, 2010 which itself claims priority to U.S. Provisional Patent Application Ser. No. 61/283,402, titled "Apparatus for Intelligent Airflow Sensors," filed on Dec. 3, 2009; and U.S. Provisional Patent Application Ser. No. 61/338,468, titled "Apparatus for Intelligent Airflow Sensors," filed on Feb. 20, 2010 and U.S. Provisional Patent Application Ser. No. 61/343,053, titled "Wind and Sound Indicator," filed on Apr. 23, 2010. Further, this application is a continuation-in-part of U.S. patent application Ser. No. 12/885,391 titled "Intelligent Air Flow Sensors," filed on Sep. 17, 2010, now abandoned which itself claims priority to U.S. Provisional Patent Application Ser. No. 61/277,289, titled "Apparatus for Intelligent Airflow Sensors," filed on Dec. 23, 2009; the contents of all of which are herein incorporated by reference in their entirety.

FIELD OF THE INVENTION

The disclosure relates generally to airflow sensors for use in spirometry, forced oscillatory techniques, impulse oscillometry and the analysis of sounds from the respiratory tract. More specifically, the disclosure relates to a sterilizable sensor for the measurement of respiratory airflow.

BACKGROUND OF THE INVENTION

Chronic obstructive pulmonary disease (COPD) affects between 15 million and 30 million Americans and is the fourth leading cause of death in the United States. COPD generally describes long-standing airway obstruction caused by emphysema or chronic bronchitis. COPD includes the class of diseases characterized by relatively irreversible limitations of airflow in the lungs. The most familiar common disease in this class of diseases is emphysema, in which the air sacs of the lung become damaged and/or destroyed, and unable to participate in air exchange. Another common respiratory disease is asthma, which is characterized by wheezing, coughing, chest tightness, and shortness of breath. Wheezing is a mid-frequency pitched, whistling or sibilant sound caused by airway narrowing due to inflammation in the airways and/or secretions in the airways. The muscles surrounding the airways become tight and the lining of the air passages swell. This reduces the amount of air that can pass by, which leads to wheezing sounds. Spirometry is a well known standard for the diagnosis and management of COPD.

Spirometry is a physiological test that measures how an individual inhales or exhales volumes of air as a function of time. The primary signal measured in spirometry may represent volume or flow. The spirometry is typically performed using a spirometer. The spirometer may provide graphs, called spirograms, as a result of the measurements. The spirograms may illustrate a volume-time curve and/or a flow-volume loop. An exemplary flow-volume loop 100 is illustrated in FIG. 1.

The most common parameters measured in spirometry are illustrated in FIG. 1. These parameters are Forced Vital Capacity (FVC), Forced Expiratory Volume at timed intervals of 0.5, 1.0, 2.0, and 3.0 seconds ($FEV_{1/2-3}$), Forced Expiratory Flow 25-75% ($FEF_{25-75\%}$), Forced Inspiratory Flow 25-75% ($FIF_{25-75\%}$) and Peak Expiratory Flow Rate (PEFR). FVC is the volume of air that can forcibly be blown out after full inhalation, measured in liters. $FEF_{25-75\%}$ is the average rate of expiratory airflow from the 25% volume point to the 75% volume point of the expiratory effort, usually expressed in liters per second. $FEF_{A\%}$ is the momentary expiratory flow rate at "A"% of maximal expiratory effort, usually expressed in liters per second. FIF is similar to FEF except the measurement is taken during inhalation. PEFR is the maximal flow (or speed) achieved during the maximally forced exhalation initiated at full inhalation, measured in liters per minute. PEFR can be measured with spirometers or with simpler mechanical or electronic peak flow meters, discussed below.

Elastic flap airflow sensors have been used in human respiratory medicine for unidirectional measurement, i.e. measurement during inhalation or exhalation, of airflow in mechanical peak flow meters. An elastic flap airflow sensor may be defined as an airflow sensor with a flow-sensing member. The flow-sensing member may be a flap positioned so that it is moved by the airflow to be measured without creating enough resistance to significantly impede the airflow to be measured. The pressure of oncoming air against the flap causes elastic displacement, typically by bending. Airflow is measured by measuring the elastic displacement or deformation of the flap. In mechanical elastic flap peak flow meters, the flap is typically made of a flat steel spring which provides low resistance to the airflow. The flap pushes a low resistance pointer along a track as the flap is displaced due to the airflow. The pointer remains at the position of maximum displacement while the flap falls back as the rate of airflow decreases. The flap returns to its "zero flow" position at the end of the expiratory effort. PEFR may be read directly from the position of the pointer at the end of the breath, after which the pointer is manually returned to the "zero" position for the next effort.

In U.S. Pat. No. 6,447,459, Larom discusses measuring human expiratory airflow using a steel spring elastic flap flow-sensing plate. In Larom, the displacement of the steel spring elastic flap is tracked using a strain gauge or other sensor types. Larom discusses mechanisms to damp the vibrations of the flap both before and after the achievement of maximum displacement. However, the solutions proposed by Larom either make the device non-portable, i.e. in the case of electromagnetic damping, or create surface irregularities, i.e. the use of lever and vanes, which can trap mucus and other respiratory secretions. As a result, Larom's device becomes difficult to clean and disinfect to meet regulatory requirements for other than single patient use. Another issue with Larom's device is that the sensor can only provide unidirectional airflow measurement, i.e. either during inhalation or exhalation. Larom's device further fails to measure sonic vibration of the pulmonary function such as lung sounds indicating abnormal lung function, i.e. wheezing. Specifically, the damping needed for Larom's sensor to accurately record the deflection of the steel spring elastic flap also damps and hence eliminates the sonic vibration.

A pneumotachometer is another conventional type of device that can be used for measuring the flow of respiratory gases. A pneumotachometer is a device to measure respiratory airflow by measuring the pressure drop across a fixed resistance. FIGS. 2A-2B illustrate conventional pneumotachometers. Specifically, FIG. 2A illustrates an exemplary Fleisch-type pneumotachometer 202 and FIG. 2B illustrates an exemplary Lilly-type pneumotachometer 208. In the Fleisch-type pneumotachometer 202, the fixed resistance is an array of capillaries while in the Lilly-type pneumotachometer 208, the fixed resistance is a partially obstructing mesh or membrane.

In the Fleisch-type pneumotachometer 202 illustrated in FIG. 2A, the flow (V') is measured in a tube with a small, fixed resistance. The resistance to flow comes from an array of capillaries 206 arranged in parallel to the direction of flow. Accurate measurements with the Fleisch-type pneumotachometer 202 are best performed when the flow pattern is laminar and the flow is linearly related to pressure drop.

In the Lilly-type pneumotachometer 208 illustrated in FIG. 2B, the flow (V') is derived from the pressure difference over a small, fixed resistance, produced by a fine metal mesh 210. Accurate measurements with the Lilly-type pneumotachometer 210 are best performed when the flow pattern is laminar and the flow is linearly related to pressure drop.

However, as indicated above, the pneumotachometers only measure the flow of respiratory gases. Thus, pneumotachometers fail to measure the sonic properties of the forced vital capacity maneuver. Moreover, the sampling rate associated with the conventional Fleisch-type and Lilly-type pneumotachometers is the standard sampling frequency of 50 Hz. This sampling rate is insufficient for measuring the sonic vibration associated with respiration, which may have components with frequencies as high as 1000 Hz or higher.

Other methods for measuring the respiratory function are the conventional Forced Oscillation Technique (FOT) and the conventional Impulse Oscillometry (IOS). FOT and IOS are techniques to measure the impedance of the airway by superimposing pressure fluctuations of known frequency and intensity on tidal breathing and analyzing the resulting perturbations of pressure and airflow. The two techniques differ in that in FOT, the superimposed pressure fluctuations are continuous and continue during measurement of the resulting flow and pressure perturbations. On the other hand, in IOS, the superimposed pressure fluctuations consist of short pulses, where the resulting perturbations are measured between pulses. The principal advantage of FOT and IOS compared to spirometry is that FOT and IOS do not depend on the performance of forced respiratory maneuvers by the patient or the source of airflow under analysis. Thus, it is possible to measure airway impedance with FOT and IOS in infants and children too young to cooperate in spirometry, in patients who are unconscious, and in non-human vertebrate animals. Disadvantages of FOT and IOS include the high cost, complexity and delicacy of presently available equipment and the consequent paucity of normative data for measurements in health and disease.

FIG. 2C illustrates an exemplary device 212 for IOS. The device 212 includes an impulse generator 214 and a pneumotachometer 216 attached to a mouthpiece 218. A metal screen 250 is provided in the pneumotachometer 216. A terminal resistor 220 and the impulse generator 214 are connected to the pneumotachometer 216 via a Y-adapter 222. A flow transducer 224 and a pressure transducer 226 are connected to the pneumotachometer 216 for measuring the flow and the pressure of the respiratory gases, respectively. The measurements of the flow transducer 224 and the pressure transducer 226 are conveyed to a digital signal processor 228. The output of the digital signal processor 228 is provided to a loudspeaker 230 and a computer 232.

The device 206 illustrated in FIG. 2C can be used in performing IOS by measuring various parameters of airway impedance as a function of pressure pulse frequency across a range from 5 to 40 Hz. The resulting signals are electronically separable from the airflow changes of spontaneous respiration, which occurs at frequencies from about 0.1 Hz to 5 Hz. As indicated above, the sonic vibration associated with respiration may have components with frequencies as high as 1000 Hz.

The device 206 illustrated in FIG. 2C may also be used for FOT if speaker output is continuous rather than pulsed. Energy may be applied at one frequency, at several frequencies in sequence, or at multiple frequencies simultaneously using pseudo-random noise. The ratio between the pressure drop across the airway and the airflow at a frequency included in the speaker output is defined as the impedance of the airway, by analogy to electrical impedance. The respiratory impedance is a complex quantity, e.g. including a real part and an imaginary part or an amplitude component and a phase component. The respiratory impedance may be used to determine the oscillatory pressure component in phase with flow and oscillatory flow amplitude.

SUMMARY OF THE INVENTION

The present invention provides a single sensor capable of detecting both airflow in spirometry, FOT and IOS, as well as the full range of sound frequencies needed to track clinically relevant breath sounds. The sensor is an elastic flap airflow sensor that is capable of detecting data needed for both spirometry and auscultation measurements.

The sensor is sterilizable and designed for the measurement of respiratory airflow. The sterilizable sensor is suitable for non-human and non-medical fluid flow metering applications as well. The sensor includes a movable flap with one or more integrated strain gauges for measuring displacement and vibration. The sensor is inherently bidirectional. Additional devices such as sensors for the ambient level of various chemicals, sensors for temperature, sensors for humidity and microphones, may be affixed to the flap. When the strain gauge is placed in a conventional Wheatstone bridge configuration, the sensor can provide the airflow measurements needed for medical spirometry.

According to an embodiment of the present invention, an airflow sensing system is provided. The airflow sensing system includes a housing, a movable flap, a sensor and a determining unit. The housing has a chamber that is sized and dimensioned to allow air generated by an air source to pass therethrough. The air from the source causes the flap to move when the air passes thereover. The sensor is coupled to the movable flap for generating an output signal when the flap moves. The determining unit receives the output signal of the sensor and in response thereto, determines an airflow rate of the air from the air source and generates a sound data signal representative of sound associated with the air and generated by the air source.

According to various embodiments of the present invention, the sensor may be configured to simultaneously sense displacement of the movable flap and vibration of the movable flap. The displacement of the movable flap is representative of airflow rate data associated with the flow of air. The vibration of the movable flap is representative of sound data associated with the flow of air.

According to various embodiments of the present invention, the airflow sensing system may also include a voltage conversion unit for receiving the output signal of the sensor and converting the output signal into a voltage output signal. The determining unit may also include an amplification unit for receiving the voltage output signal and generating an amplified voltage output signal. The determining unit may also include an air flow rate determining unit and a sound determining unit. The airflow rate determining unit may receive the amplified voltage output signal and determine in response thereto the air flow rate of the air from the air source based at least in part upon the output signal of the sensor. The sound determining unit may receive the amplified voltage output signal and generate in response thereto the sound data signal representative of the sound associated with the air and generated by the air source. The sound determining unit may also include a sound processing unit for generating the sound data signal in response to the amplified voltage output signal. The sound determining unit may also include a frequency conversion unit for receiving the sound data signal and in response thereto converting the signal into a frequency signal.

According to various embodiments of the present invention, the air flow rate determining unit may include a converter and a calculation unit. The converter may convert the amplified voltage output signal into a digital output signal. The calculation unit may determine the air flow rate of the air based upon the digital output signal.

According to various embodiments of the present invention, the airflow sensing system may also include an air flow rate determining unit for determining the air flow rate of the air from the air source based at least in part upon the output signal of the sensor. The airflow sensing system may further include a sound determining unit for generating the sound data signal representative of the sound associated with the air and generated by the air source.

According to another embodiment of the present invention, method for simultaneously determining airflow rate and sound data of air generated by an air source using a single sensor is provided. The method includes providing a sensor coupled to a movable flap that moves when air from an air source passes thereover, wherein the sensor generates an output signal when the movable flap moves. The method also includes receiving the output signal of the sensor and determining an airflow rate of the air from the air source. The method further includes generating a sound data signal representative of sound associated with the air and generated by the air source.

According to various embodiments of the present invention, the method may also include simultaneously sensing displacement of the movable flap and vibration of the movable flap using the sensor, wherein the displacement of the movable flap is representative of airflow rate data associated with the flow of air and the vibration of the movable flap is representative of sound data associated with the flow of air. The method may also include determining the air flow rate of the air from the air source based at least in part upon the output signal of the sensor. The method may further include generating the sound data signal representative of the sound associated with the air and generated by the air source. The output signal may be converted into a digital output signal. The air flow rate of the air may be determined based upon the output signal. The sound data signal may be generated in response to the output signal.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 8A illustrates an exemplary three dimensional plot representing auscultation data gathered using the airflow measuring device of the present invention;

DETAILED DESCRIPTION OF THE INVENTION

Present invention provides an airflow sensor that is capable of measuring bidirectional airflow of a patient, as well as clinically relevant breath sounds associated therewith. Breath sounds include sounds that are associated with inhalation and exhalation of humans and/or animals. Specifically, the airflow sensor used according to the teachings of the present invention is capable of simultaneously detecting auscultation data and airflow data. The airflow sensor generates an output signal in response to the presence of airflow. The generated output signal is representative of both the airflow data including airflow rate, and the breath sound data associated therewith.

According to various embodiments of the present invention, a single sensor is provided for sensing both the airflow in spirometry and the full range of sound frequencies needed to track clinically relevant breath sounds in auscultation. Any suitable type of sensor can be used provided it is capable of sensing both airflow and breath sounds while simultaneously providing an appropriate output signal that is representative of or can be correlated to the patient's airflow and breath sounds. Examples of sensors suitable for this purpose include strain gauges and piezoresistive or piezoelectric sensors. According to a preferred embodiment, the present invention employs a thin film sensor mounted in an airflow chamber. The thin film sensor may be a piezoresistive sensor that is sensitive to bending. An amplified signal output from the sensor consists of a direct current (DC) electrical component that measures airflow (spirometry) and a high frequency alternating current (AC) audio component that is representative of sound from the lungs (auscultation) during the inhalation and exhalation cycles of respiration.

Particular implementations of the present invention may provide one or more of the advantages provided herein. The airflow sensor described in the present application not only overcomes the above-listed limitations of conventional spirometers but also provides the simultaneous, direct sensing or detection of sound from the airway.

The piezoresistive airflow sensor of the present invention may also be used in connection with the conventional FOT or IOS instrumentation to replace the pneumotachometer airflow sensors. Thus, it is possible to produce FOT or IOS instruments at lower cost. Replacing the pneumotachometer of the conventional FOT or IOS instrumentation with the piezoresistive airflow sensor of the present invention results in a more stable, portable, easier to use and easier to maintain FOT or IOS device. The simpler design and greater stability in the FOT or IOS device afforded by the present invention allows the FOT or IOS device to enter the mainstream of clinical medicine.

Figure 3:
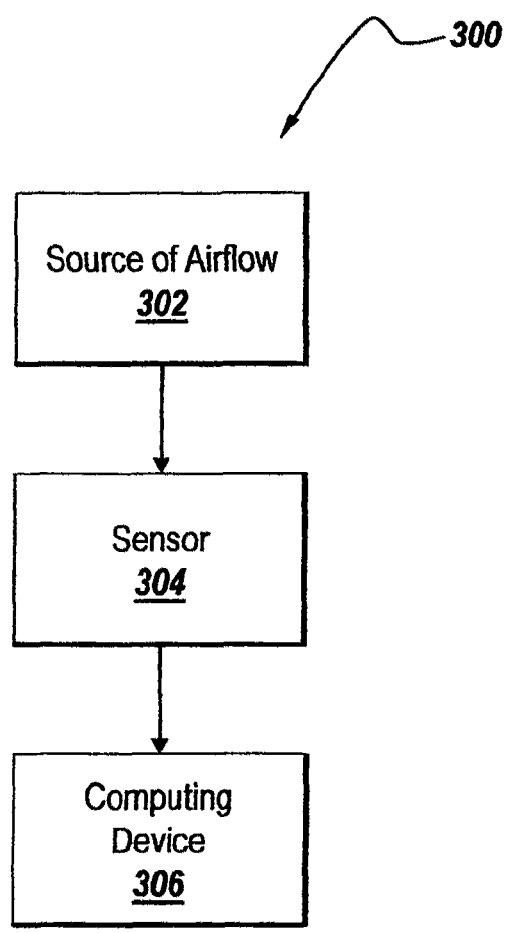
FIG. 3 is a general block diagram view of a system for measuring airflow and breath sounds according to the techniques of the present invention.

FIG. 3 is a schematic block diagram of a system 300 for generally measuring, collecting, analyzing, processing and/or gathering airflow and sound data. If configured for task-appropriate data analysis, the system 300 may be used for any of spirometry, FOT or IOS. The system 300 includes the sensor 304 of the present invention. The sensor 304 is connected to a source of airflow 302 to be analyzed. The airflow can be provided, for example, by a patient. The sensor 304 may be provided in a mouthpiece that allows measuring characteristics of the air flowing in and out of the lungs of the source of airflow 302. The readings of the sensor 304 may be sent to a computing device or system 306 for further analysis. The computing device 306 may include one or more processors, one or more storage devices, or one or more filters or other associated processing circuitry, and a display device. The various components of the computing device 306 can be located in a single location or can be distributed throughout the system 300. The illustrated computing device processes the output signal generated by the sensor 304 and is capable of determining the airflow rate and breath sounds associated with the source 302.

Figure 4A:
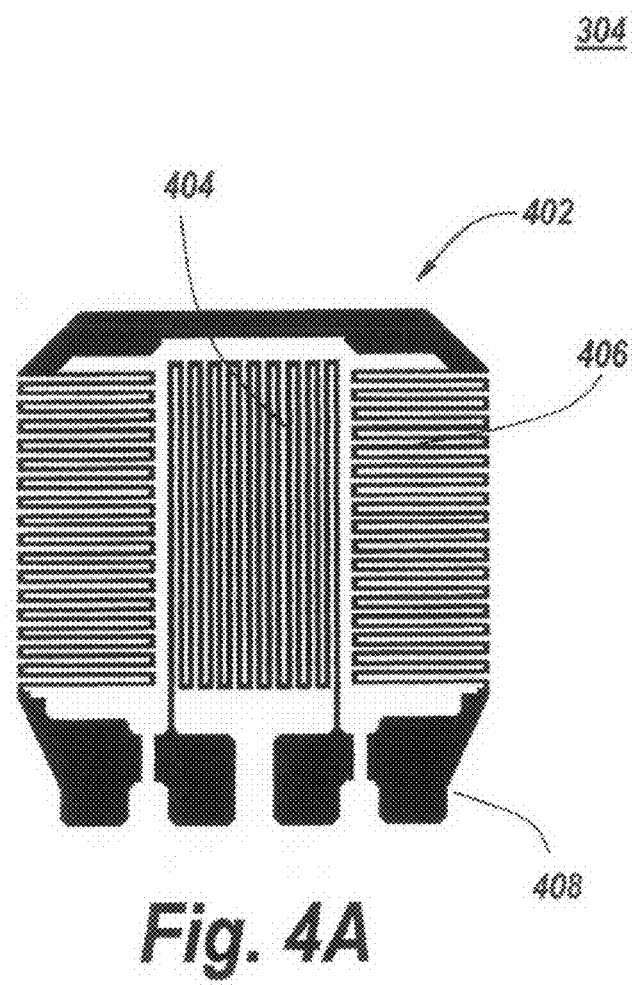
FIG. 4A is a schematic depiction of an exemplary airflow sensor according to an exemplary embodiment of the present invention.

FIG. 4A is a general schematic depiction of an exemplary sensor 304 according to one embodiment of the present invention. Specifically, FIG. 4A illustrates a piezoresistive sensor 402 that has two orthogonal piezoresistive circuits 404, 406 for measuring both sound and spirometry data. The resistance of both circuits may be about 120 ohms.

The inner circuit 404 may be sensitive to spirometry data while the outer circuit 406 may be sensitive to high frequency sounds. The sensor 304 of the present invention may be sensitive to sounds with frequencies between about 1 Hz and about 1000 Hz. Preferably, the sensor 304 of the present invention is sensitive to sounds with frequencies between about 35 Hz and about 1000 Hz. A plurality of pads 408 are provided at a lower end of the sensor 402 for connecting the sensor 402 to other system circuitry.

The piezoresistive sensor 402 illustrated in FIG. 4A is provided for illustrative purposes only and should not be construed in a limiting sense. The sensor 304 of the present invention may also employ a single piezoresistive circuit that is sensitive to both spirometry data and high frequency sounds.

The sensor 402 used in the present invention may consist of a grid of metallic wire bonded to polyimide or polymer films such as polyethylene terephthalate (PET), nylon, polypropylene or polyethylene. The metallic wire may be made of constantan, i.e. a copper-nickel alloy consisting of about 55% copper and 45% nickel. Constantan has a resistivity that is constant over a wide range of temperatures. Alternatively, the metallic wire may be made of gold, chromium, aluminum, etc. Aluminum or steel has much less flexibility than constantan.

The piezoresistive sensor 402 may be constructed by deposition techniques, for example, vacuum deposition, electroplating, and printing procedures familiar in the semiconducting fabrication field. FIG. 4A illustrates an exemplary pattern of constantan deposited on polyimide for measuring strain in two perpendicular directions. As provided above, the sensor 402 of the present invention may be formed by depositing constantan in polyimide in a single direction. The metallic wire may be deposited on polyimide using E-beam or sputtering deposition techniques. Photolithography mask, shadow masks, and electrophotographic imaging may be used in conjunction with E-beam deposition techniques in manufacturing the strain gauge. Optionally, various coatings may be applied to the strain gauge for protecting the circuit from oxidation or water aging.

Conventionally, a polyimide-backed strain gauge is used to measure the strain of a carrier medium such as a piece of aluminum, or steel, to which the polyimide flap is glued. When the carrier medium is strained, the length of the grid changes, which causes a change in the electrical resistance. A Wheatstone bridge may used to monitor the change in resistance and produce an output voltage proportional to the strain in the carrier medium.

Contrary to the conventional strain gauges where the gauge is glued directly onto the carrier medium, in producing the airflow sensor of the present invention, the sensor is attached to the carrier medium at one end. Thus, the sensor becomes integrated with a bendable flap. In the present invention, the polyimide flap itself is the target of the measurement.

Figure 4B:
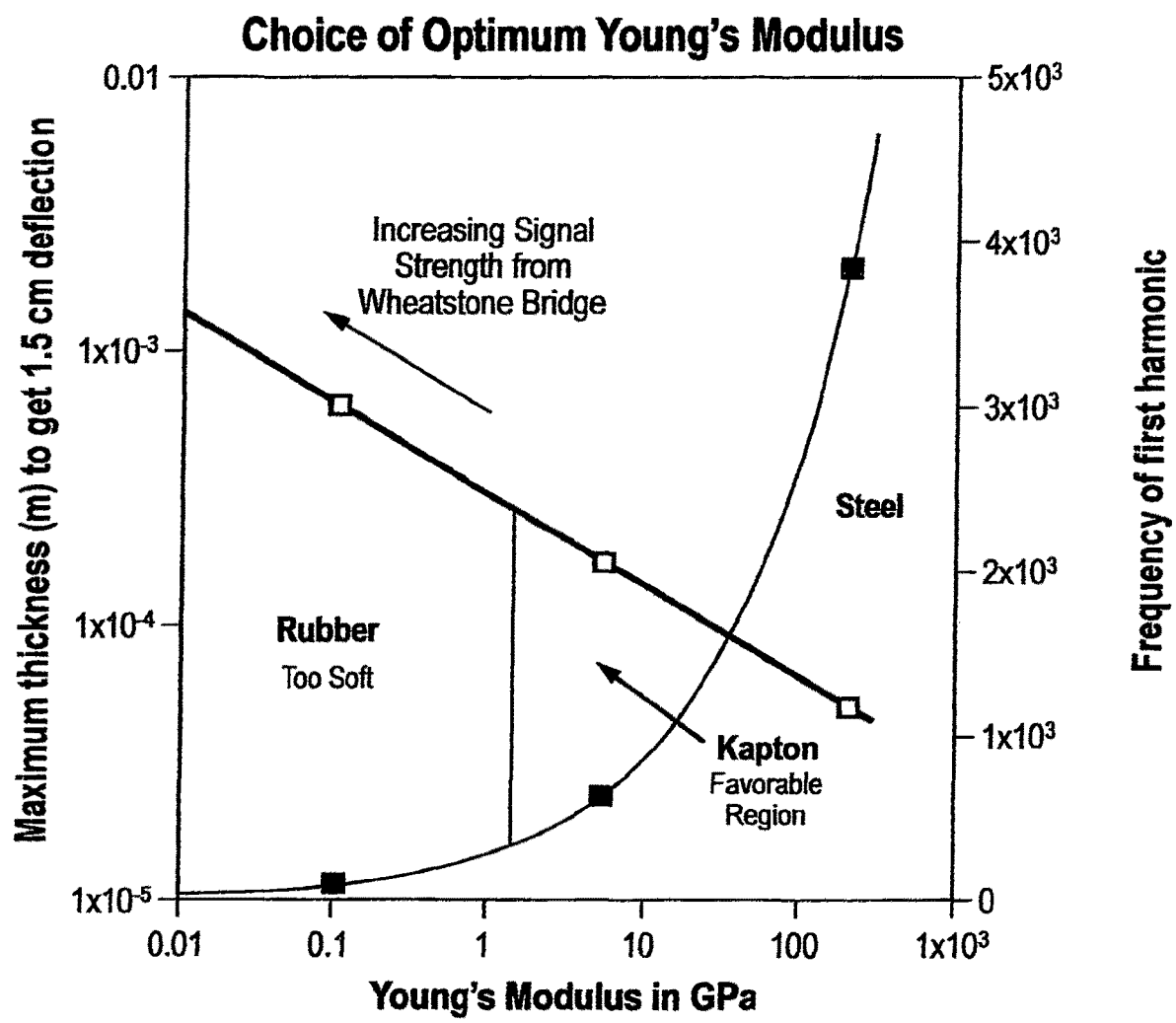
FIG. 4B is a graphical depiction of an exemplary mode analysis examining the effect of Young's modulus on the frequency of a first vibrational mode of an exemplary sensor and according to the teachings of the present invention.

According to various embodiments of the present invention, Kapton may be used as the carrier medium for the sensor. Kapton is a polyimide film that remains stable in a wide range of temperatures, i.e. from −269 to +400° C. (−452 to 752° F.). FIG. 4B illustrates a mode analysis examining the effect of Young's modulus on the frequency of the first vibration mode of the sensor using a one dimensional model. FIG. 4B further illustrates the thickness of a backing required to obtain a 1.5 cm deflection. For a given pressure, stiff materials, such as steel, need to be very thin. For such materials the frequency of the first vibration mode is high. Softer materials, such as rubber, have a lower frequency but are generally thicker. Thicker materials are desirable since a larger signal is observed from the sensor. The present inventors have realized that a reasonable compromise between the two extremes is found where the two curves intersect on FIG. 4B. The intersection point illustrates the properties of Kapton.

Kapton is a polymer that has a glass transition temperature of greater than 350° C., a coefficient of thermal expansion of $12 \times 10^{-6}$/° C., and a RMS surface roughness of approximately 30 nm for the film. Kapton polyimide films have low shrinkage properties, i.e. a 75 µm thick foil shrinks approximately 0.04% after about 2 hours at about 200° C. The film has a relatively low humidity expansion coefficient of $9 \times 10^{-6}$/% RH, a water permeability of 4 $g/m_2$/day, oxygen permeability of 4 $cm_3/m_2$/day, and water absorption of 2.4%. The bulk modulus of Kapton E is 780 Kpsi.

However, the use of Kapton in accordance with the present invention is for illustrative purposes only and should not be construed in a limiting sense.

Figure 4C:
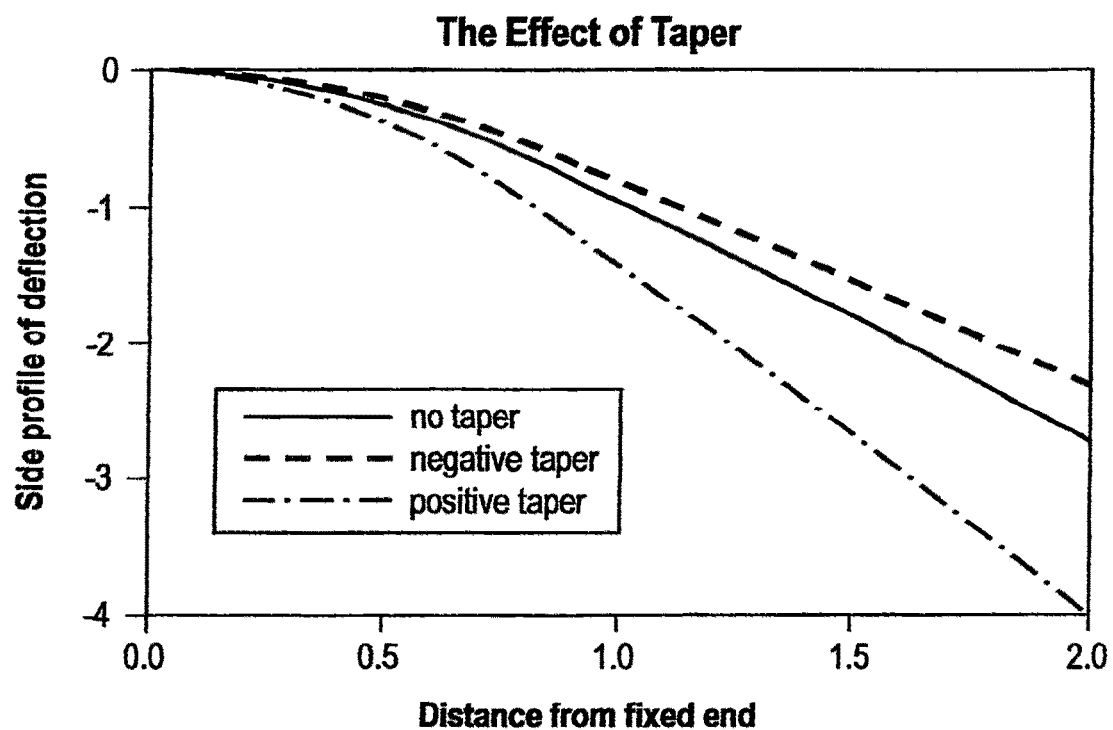
FIG. 4C is a graphical depiction of the effects of a tapered design during bending of an exemplary flap used in the system of FIG. 3 according to the teachings of the present invention.

According to various embodiments of the present invention, the flap 450 may be a tapered surface. FIG. 4C graphically depicts the performance of the flap with and without a taper. Specifically, the graphical lines illustrate how the side profiles of the flaps bend under pressure. A positive taper can be used in connection with the present invention. A flap with a positive taper has a fixed end that is thicker than the free end. A flap with a negative taper has a free end that is thicker than the fixed end. During bending, the maximum curvature that is proportional to change in resistance occurs at the fixed end. As illustrated in FIG. 4C, larger signals are generated using a flap with a positive taper rather than using a flap with no taper.

Figure 4D:
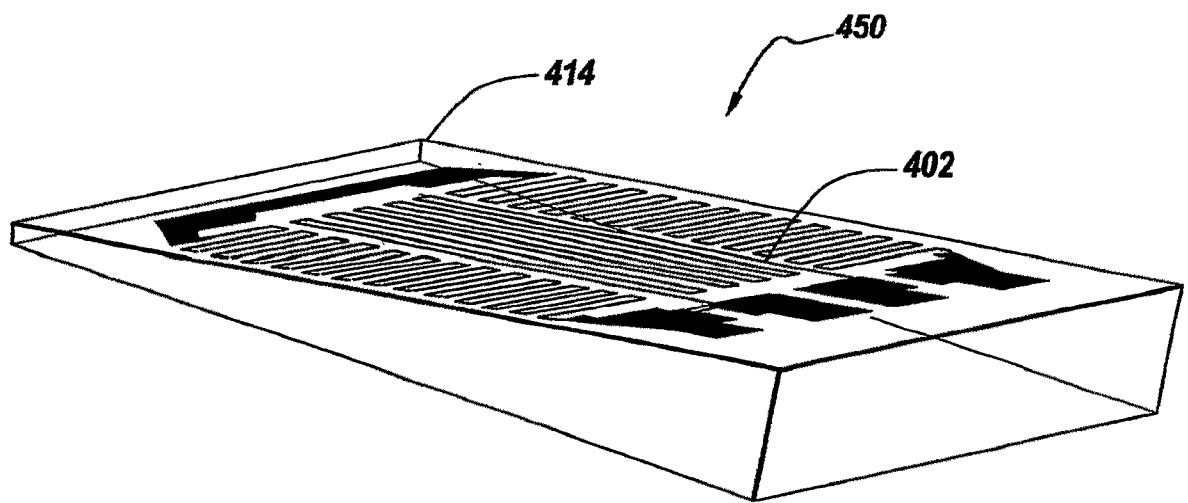
FIG. 4D illustrates an exemplary sensor mounted on a tapered surface according to an exemplary embodiment of the present invention.
Figure 5:
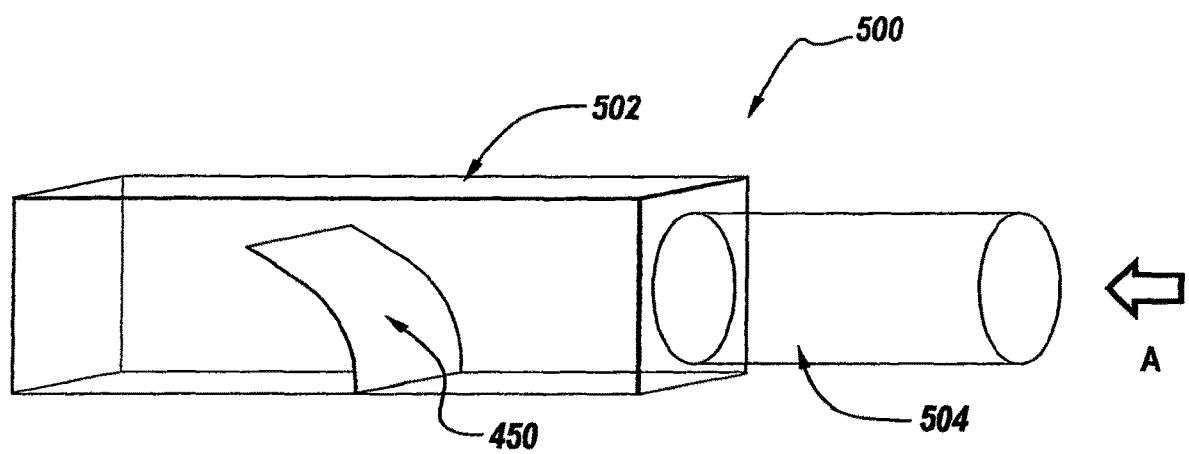
FIG. 5 is a perspective view of a device that captures spirometry data and breath sounds simultaneously according to the teachings of the present invention.
Figure 6A:
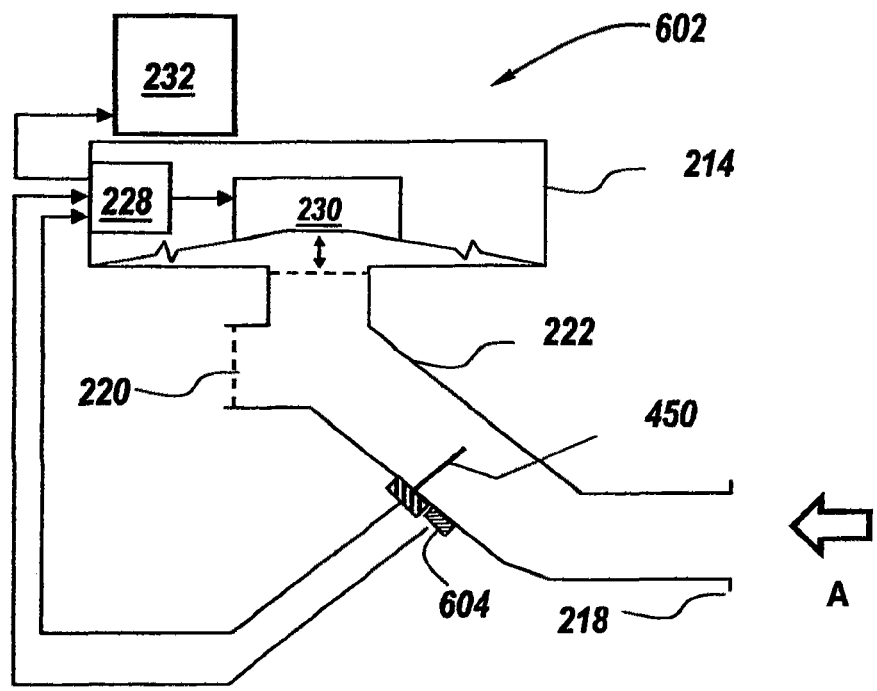
FIG. 6A is a schematic depiction of an exemplary FOT or IOS device that employs a piezoresistive airflow sensor and a pressure sensor according to the teachings of the present invention.
Figure 6B:
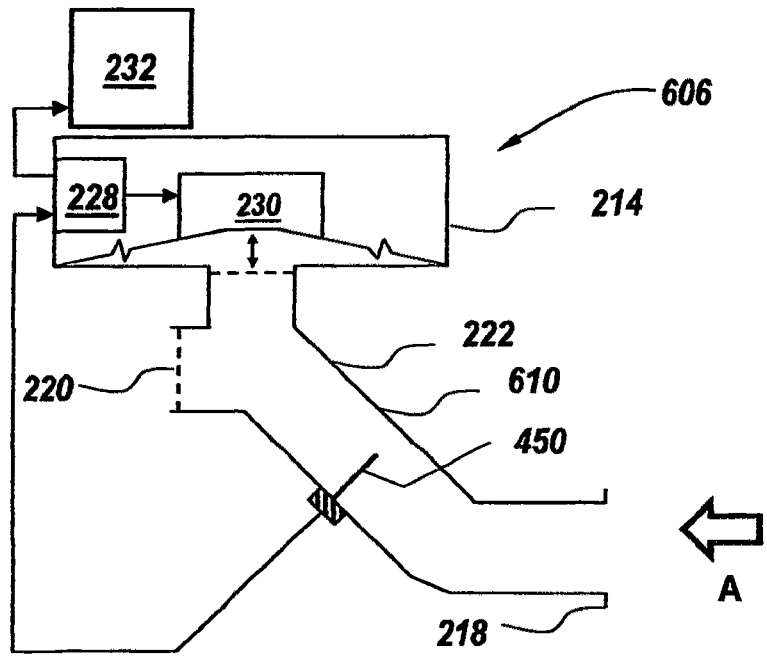
FIG. 6B is a schematic depiction of another exemplary FOT or IOS device that employs only the piezoresistive airflow sensor according to the teachings of the present invention.

FIG. 4D illustrates an exemplary sensor 402 mounted on or affixed to a tapered surface 414 of the flap 450 according to an embodiment of the present invention. The flap 450 formed according to FIG. 4D may be used in a device to detect and/or capture spirometry data and breath sounds simultaneously. Such an exemplary device is illustrated in FIG. 5. The flap 450 may also be used in connection with FOT or IOS devices, as illustrated in FIGS. 6A-6B.

Figure 4E:
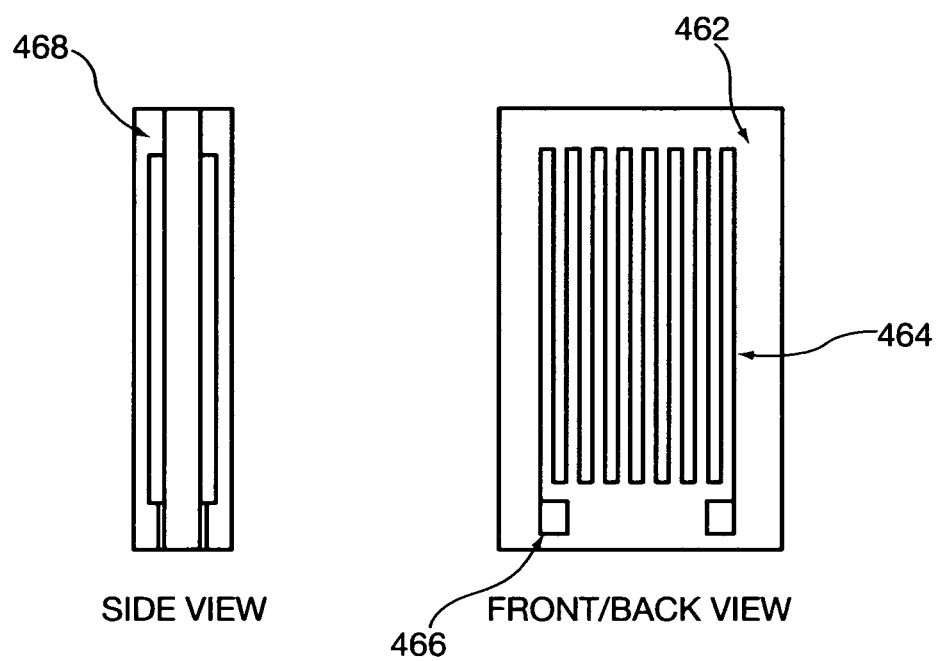
FIG. 4E illustrates an exemplary pair of symmetric sensors mounted on a tapered surface according to an exemplary embodiment of the present invention.

FIG. 4E illustrates an alternative exemplary sensor, in particular a symmetric sensor 460. In this sensor, substrate 462 is coated with metal 464 on both sides of the flap. Coating 468 may then be applied to provide further structural integrity and protection for the deposited metal. Ideally, this sensor is completely balanced, positionally, on the flap substrate, i.e. the metal is deposited symmetrically with regard to side-to-side and front-to-back dimensions. Pads 466 are provided for electrical connection to the sensor. The metal of this sensor may be deposited by any of a number of techniques such as sputtering, e-beam, and thermal evaporation. Symmetric sensors may be more reliable than non-symmetrical sensors, for example where elastic stretching of the flap occurs in response to air pressure, whereby measurement by a single sensor, placed on one side of the flap may be distorted. This is particularly so where multiple axes of stretching and bending of the flap are caused by the airflow. This is so in both the case of using either a single sensor or array of sensors on one side of the flap. Greater accuracy may therefore result with a symmetrical sensor in which the signal from the piezoresistive element(s) on the up-wind side, which are subject to both bending stretch and longitudinal stretch, are compared with signals from a piezoresistive element(s) on the opposite side of the flap, which may not be subject to each and every stretching component. Alternatively, or in combination, the sensed signals from the "back-side" sensor(s) may at least be used to compensate for such stretching through comparative signal analysis.

FIG. 5 illustrates an exemplary airflow sensing device 500 that captures spirometry data and breath sounds simultaneously. The device 500 includes an airflow chamber 502 attached to a mouthpiece 504. The airflow chamber 502 is illustrated as a rectangular chamber in FIG. 5 for illustrative purposes only. Those of ordinary skill in the art will readily recognize that the airflow chamber 502 may have any suitable shape, length or size, including but not limited to a circular chamber. The flap 450 includes a thin film sensor 402 and is provided within the airflow chamber 502. As illustrated, the flap 450 is mounted to a wall of the chamber and extends outwardly therefrom into the chamber 502. The flap 450 is positioned so as to be transverse or perpendicular to the direction of airflow, indicated by arrow A.

As illustrated in FIG. 4D, the flap 450 can have a positive or a negative taper. Specifically, the airflow sensing device 500 simultaneously measures the airflow by measuring the displacement of the flap 450 and the sound by measuring the vibration of the flap 450. The device 500 may be used in diagnosing and monitoring lung diseases or conditions that are associated with changes in spirometry values and characterized by abnormal lung sounds.

Figure 7A:
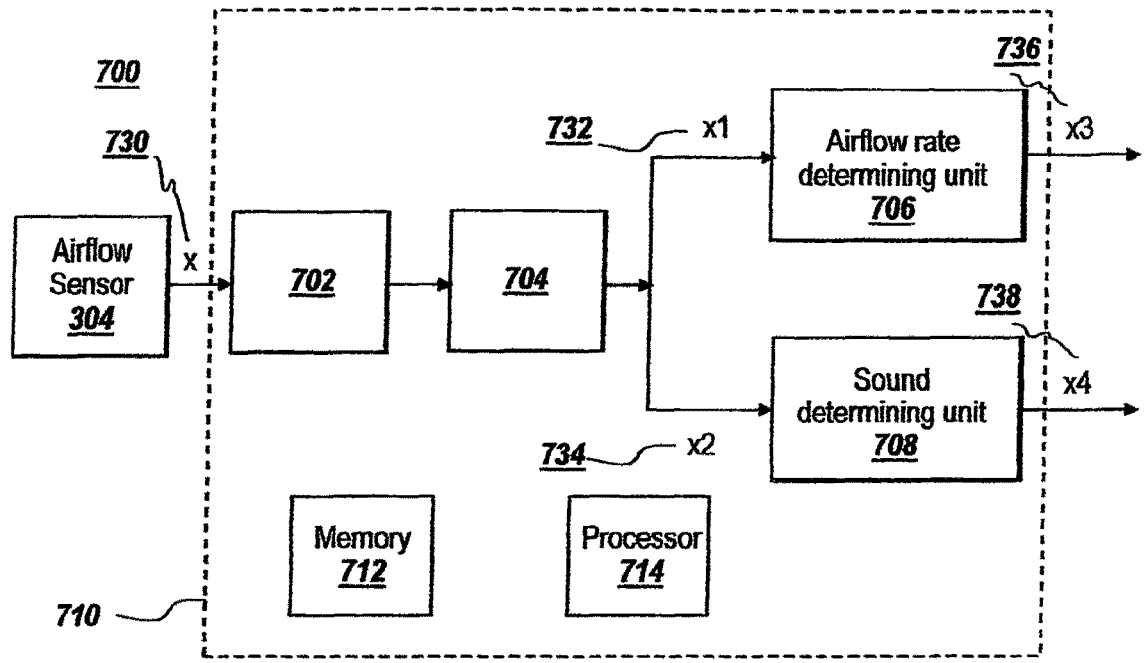
FIGS. 7A-7C are a schematic block diagram of a system where the airflow measuring device of the present invention is used to gather and analyze spirometry data and breath sounds simultaneously.
Figure 7B:
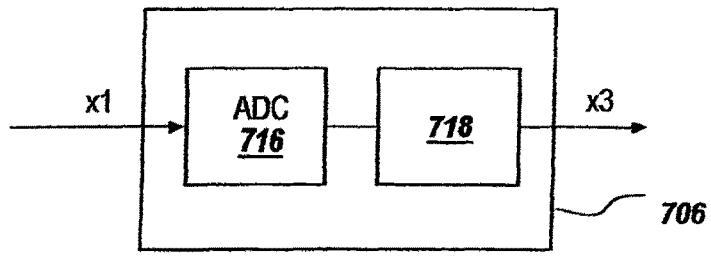
Figure 7C:
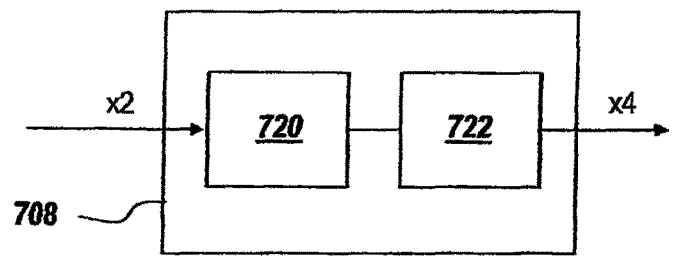

According to an exemplary embodiment, the device 500 may be used by a patient to analyze the spirometry and auscultation data. The patient breaths into device 500 through the mouthpiece 504. The inhalation or the exhalation of the patient creates an airflow in the direction A illustrated with the arrow in FIG. 5. The airflow displaces and vibrates the flap 450 in the airflow chamber 502. The displacement and the vibration of the flap 450 are sensed by the sensor (not shown) provided on the flap 450. The sensor generates an output signal that represents data associated with the displacement and the vibration of the flap 450. The data associated with the displacement of the flap 450 is used to measure airflow characteristics for spirometry analysis. The data associated with the vibration of the flap 450 is used to measure breath sound characteristics for auscultation analysis. The processing of the output signal is illustrated in FIGS. 7A-7C and is discussed below.

As indicated above, the flap 450 of the present invention may also be used in connection with FOT or IOS devices, as illustrated in FIGS. 6A-6B. FIG. 6A illustrates an airflow sensing device 602 for FOT or IOS applications. The sensing device 602 includes an exemplary piezoresistive sensor 304 according to an embodiment of the present invention. The piezoresistive sensor is coupled to the flap 450 and is similar to the flap 450 illustrated in FIGS. 4D and 5. The piezoresistive sensor 304 replaces the pneumotachometer 216 and the flow transducer 224. Pressure transducer 604 may employ different technology than pressure transducer 226 of the conventional FOT or IOS device 206.

The piezoresistive sensor 304 of the present invention functions as one branch of the Wheatstone bridge from which the voltage output feeds into an analogue-digital converter incorporated into the digital signal processor 228. The digital signal processor 228 may also include the Wheatstone bridge and amplifiers. The piezoresistive sensor-based FOT or IOS device 602 is capable of the full range of measurements that can be performed with the conventional FOT or IOS device 206. In addition, according to various embodiments of the present invention, the piezoresistive sensor-based FOT or IOS device 602 is capable of measuring impulse frequencies greater than 50 Hz, for example frequencies up to 1000 Hz. The piezoresistive sensor-based FOT or IOS may measure impulse frequencies between about 1 Hz and about 1000 Hz. More preferably, the piezoresistive sensor-based FOT or IOS may measure frequencies of between about 35 Hz and about 1000 Hz. The piezoresistive sensor-based FOT or IOS device 602 is less expensive to build and maintain, more rugged and portable, easier to clean, and simpler to operate than the conventional FOT or IOS device 206.

According to an illustrative example, the FOT or IOS device 602 may be used by a patient for collecting data for FOT or IOS applications. The patient may breath through the mouthpiece 218 provided at one end of the FOT or IOS device 602. The breathing generates airflow in the direction of the arrow A, as illustrated in FIG. 6A. The flap 450 including the sensor 304 of the present invention is provided in a direction substantially perpendicular to the direction of the airflow. The airflow causes the flap 450 to move and vibrate. The sensor 304 provided on the flap 450 senses the movement, i.e. displacement, and vibration of the flap 450. The sensor 304 generates an output signal that is representative of the displacement data and the vibration data of the flap 450. The displacement data is correlated with the airflow characteristics, such as airflow rate, of the airflow. The vibration data is correlated with the breath sound characteristics associated with the airflow. The output signal of the sensor 304 is then sent to digital signal processor 228 and a computer 232 for further processing. The processing of the output signal is discussed below in connection with FIGS. 7A-7C. FOT or IOS device 602 also includes a pressure sensor 604 that collects pressure data generated by the airflow. The pressure data is also sent to the computer 232 for processing. The pressure data collected by the pressure sensor 604 may be used for calculating impedance of the respiratory flow.

According to various embodiments of the present invention, the sensor 304 of the present invention may be used to measure the response of the airway to perturbations other than the series of short pressure pulses used in IOS and continuous waves in FOT.

Figure 1:
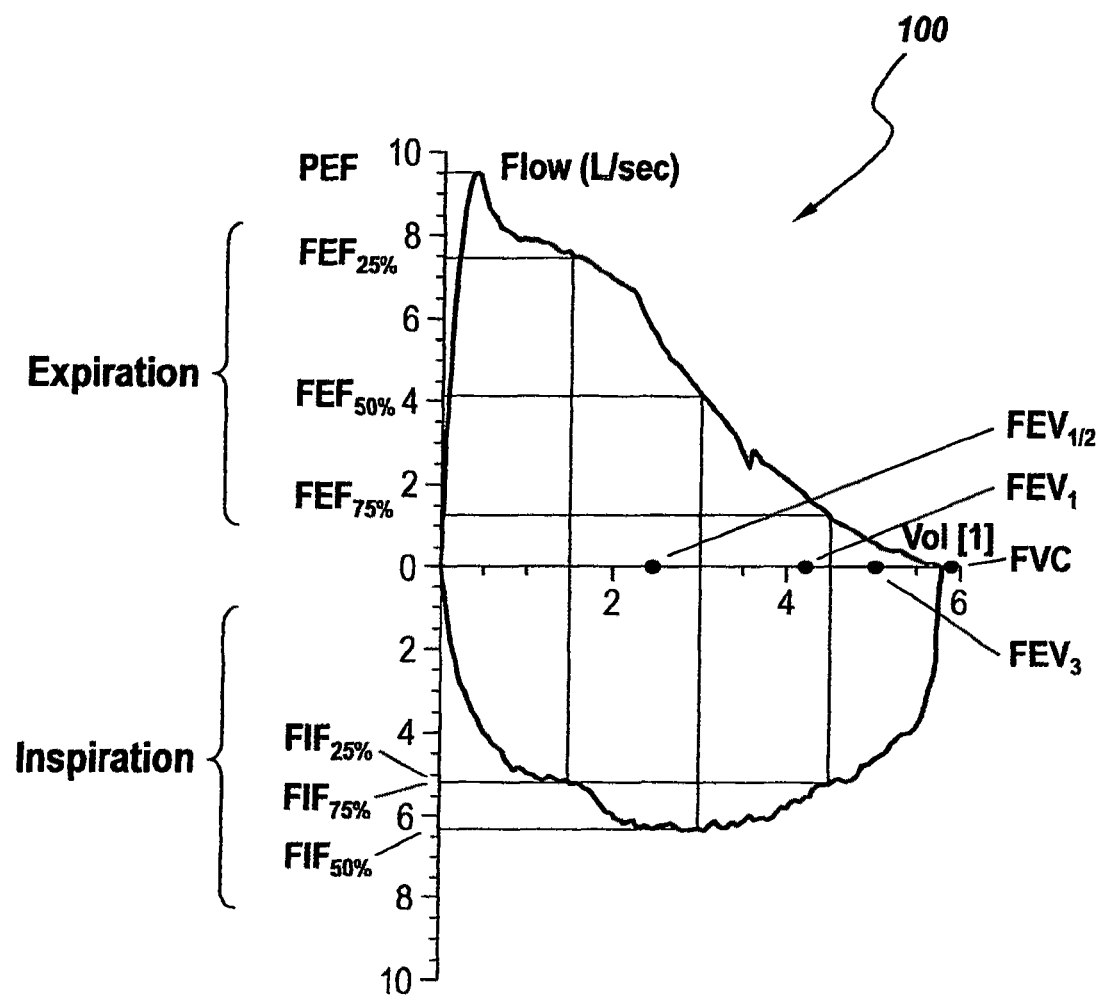
FIG. 1 is a graphical depiction of a conventional spirometry flow-volume loop.
Figure 2A:
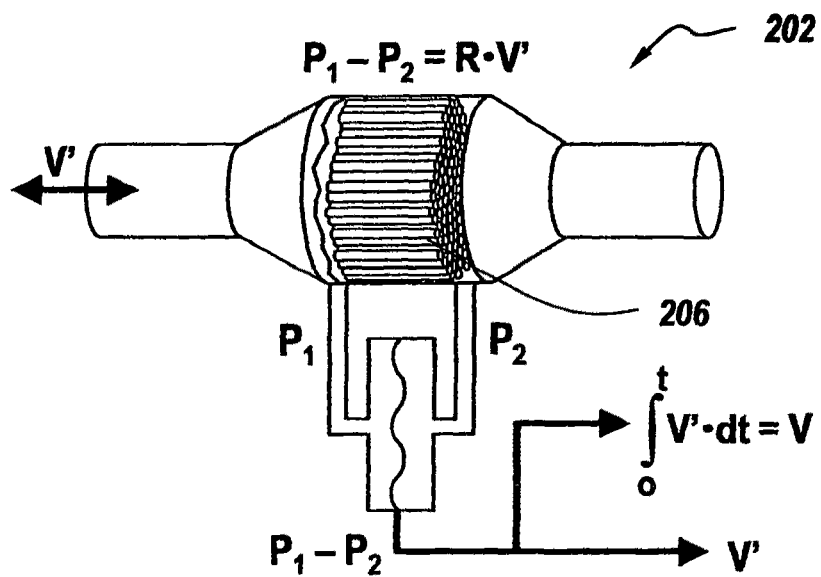
FIG. 2A is a schematic view of a conventional Fleisch-type pneumotachometer.
Figure 2B:
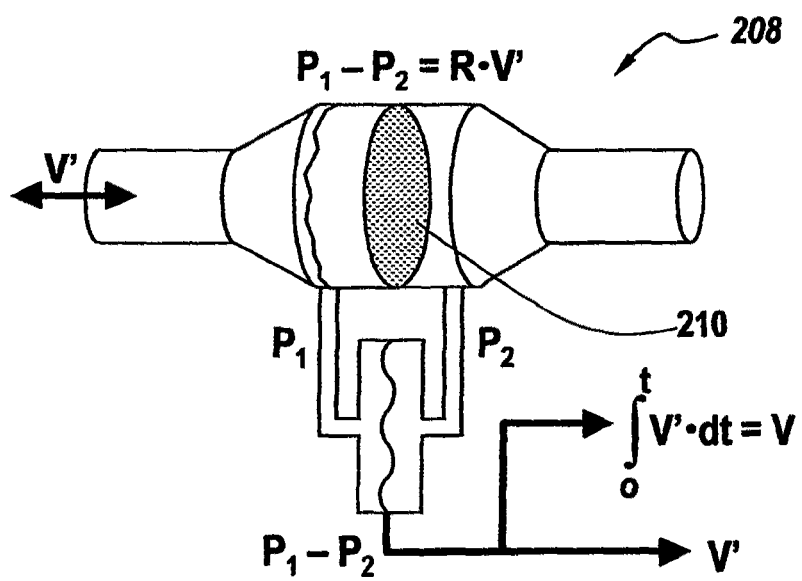
FIG. 2B is a schematic view of a conventional Lilly-type pneumotachometer.
Figure 2C:
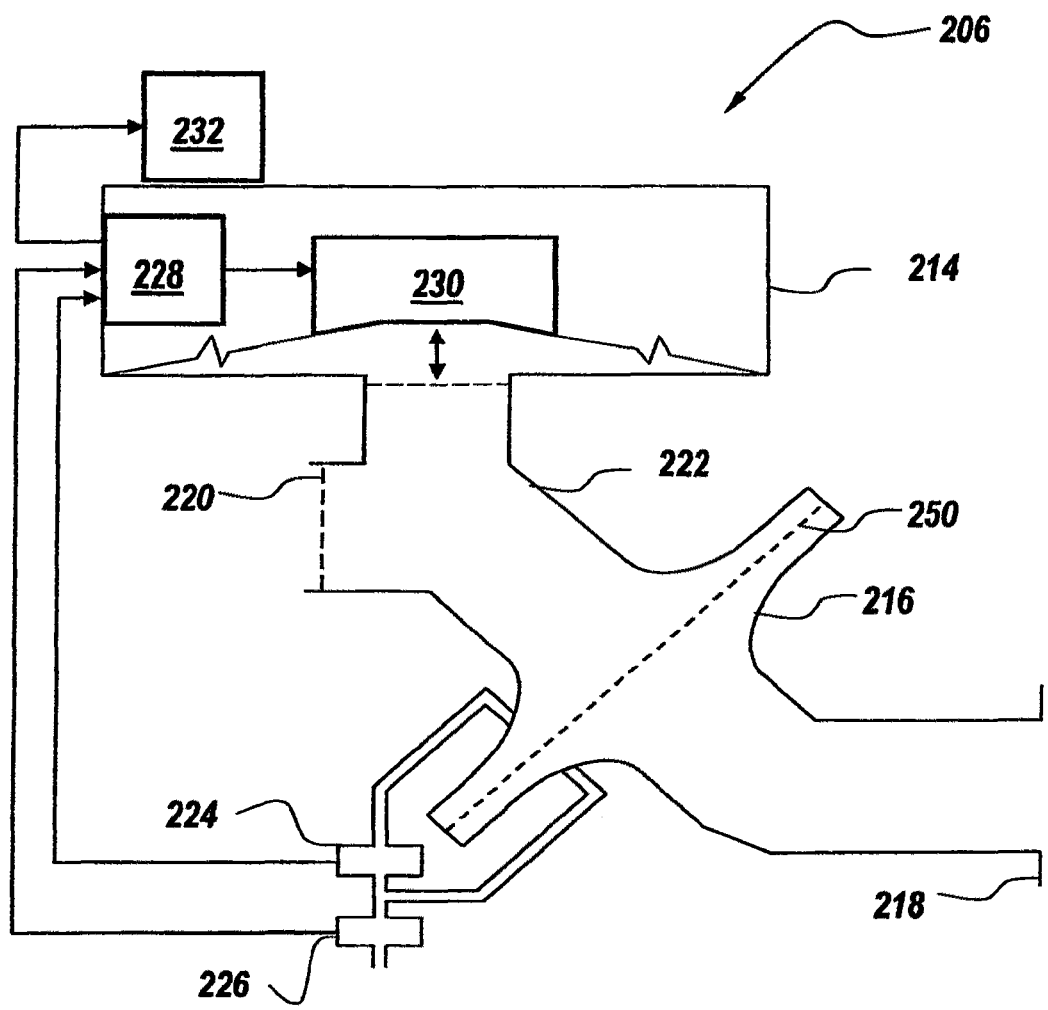
FIG. 2C is a schematic view of a conventional device for performing FOT or IOS techniques.

The sensing device 606 illustrated in FIG. 6B is a simpler version of the device 602 illustrated in FIG. 6A in that it does not include the pressure sensor 604. The piezoresistive sensor 304 of the FOT or IOS device 606 may detect airflow velocity and, therefore, differences in pressure. Accordingly, the impedance of the respiratory flow may be calculated using the data from the piezoresistive sensor 304 provided in the FOT or IOS device 606. In the sensing device 606, the pressure may be measured using the sensor 304. That way, the sensing device 606 is capable and adapted to measure the impedance inside the airway 610, for example at a central point of the airway 610. The measurement of impedance is more accurate when the measurement is taken at a location closer to the air source. Accordingly, the sensing device 606 of FIG. 6B may provide better and more accurate measurements compared to the device 206 illustrated in FIG. 2C.

The FOT or IOS device 606 can be used for the calculation of impedance of the spontaneous breathing and the superimposed impulse signal. Using the FOT or IOS device 606, it is possible to determine the phase, frequency, and signal strength at two physical points, i.e. the sensor 304 and the loudspeaker 230. The sensor and/or the flap 450 may contain additional elements such as additional parallel and/ or perpendicular strain gauge sensor 402. The additional elements of the sensor 304 may detect additional data streams from detectors such as flexible membrane pressure sensors.

According to an illustrative example, the FOT or IOS device 606 may be used by a patient for collecting data for FOT or IOS applications. The patient may breath through the mouthpiece 218 provided at one end of the FOT or IOS device 606. The breathing generates airflow in the direction of the arrow A, as illustrated in FIG. 6B. The flap 450 including the sensor 304 of the present invention is provided in a direction substantially perpendicular to the direction of the airflow. The airflow causes the flap 450 to move and vibrate. The sensor 304 provided on the flap 450 senses the movement, i.e. displacement, and vibration of the flap 450. The sensor 304 generates an output signal that is representative of the displacement data and the vibration data of the flap 450. The displacement data is correlated with the airflow characteristics, such as airflow rate, of the airflow. The vibration data is correlated with the breath sound characteristics associated with the airflow. The sensor 304 of the FOT or IOS device 606 may also sense a pressure differential caused by the airflow. Therefore, the output signal of FOT or IOS device 606 may also represent the pressure data associated with the airflow. The output signal of the sensor 304 is sent to digital signal processor 228 and a computer 232 for further processing. The processing of the output signal is discussed below in connection with FIGS. 7A-7C.

According to various embodiments of the present invention, the piezoresistive circuits 404 and 406 may be used in combination for phase calibration allowing quadrature detection. Semiconductor pressure sensors may also be incorporated in the base of the sensor 304 that may be used for reference.

FIG. 7A illustrates an exemplary sensing system 700 where the sensor 304 of the present invention is used to gather and analyze spirometry data and sound data associated with the airflow simultaneously. The sensor 304 outputs a signal x 730 that represents two sets of data simultaneously, i.e. the spirometry data x1 (732) and the sound data associated with the airflow x2 (734). The output x of the sensor 304 is sent to a voltage conversion unit 702. According to an embodiment of the present invention, the voltage conversion unit 702 may be a Wheatstone bridge. The output of the voltage conversion unit 702 is then sent to an amplification unit 704, such as an amplifier. The output of the amplifier represents two sets of converted and amplified data, i.e. the spirometry data x1 (732) and the sound data associated with the airflow x2 (734).

The spirometry data x1 (732), i.e. the displacement of the flap 450 carrying the sensor 304, may be provided to an airflow rate determining unit 706. The output x3 (736) of the airflow rate determining unit 706 represents the airflow data, i.e. the spirometry data. The sound data x2, i.e. the vibration of the flap 450 carrying the sensor 304, may be provided to a sound determining unit 708. The output x4 of the sound determining unit 708 represents the sound data, i.e. the auscultation data. The airflow determining unit 706 and the sound determining unit 708 may be a part of a determining unit 710. The determining unit 710 may include a processor 714 for performing various computations and analysis using the output x of the sensor 304. The determining unit 710 may also include a memory 712 for storing the airflow data, the sound data and/or the results of the analysis performed on the airflow data and/or the sound data. The determining unit can include other circuitry or components as would be obvious to one of ordinary skill in the art.

FIG. 7B illustrates the airflow rate determining unit 706 of FIG. 7A. The airflow rate determining unit 706 includes an analog-to-digital converter (ADC) 716. The spirometry data x1, typically an analog signal, is input to the ADC 716. The output of the ADC 176 is a DC voltage that may be coupled to a calculation unit 718. The calculation unit 718 correlates the input data signal with a pre-determined calibration curve to determine the airflow rate. The calculation unit 718 generates graphical representations of the input data and/or the results of correlating the input data with the pre-determined calibration curve. These results can be displayed on an associated display device (not shown), or can be stored in memory 712.

FIG. 7C illustrates the sound determining unit 708 of FIG. 7A. The sound determining unit 708 includes a sound processing unit 720. According to various embodiments of the present invention, the sound processing unit 720 may be a sound card. The sound data x2 is input to the sound processing unit 720. The output of the sound processing unit 720 is a sound data signal representative of the sound generated by the source of the airflow (i.e., the patient). The sound data signal is then passed through a frequency conversion unit 722. The frequency conversion unit 722 may apply Fast Fourier Transform (FFT) technique to the sound data signal. The output from the frequency conversion unit 722 may be used to determine peak frequencies that are representative of medical conditions. Accordingly, using the output of the frequency conversion unit 722, it is possible to determine whether a patient has a medical condition, such as asthma and the like.

Figure 8B:
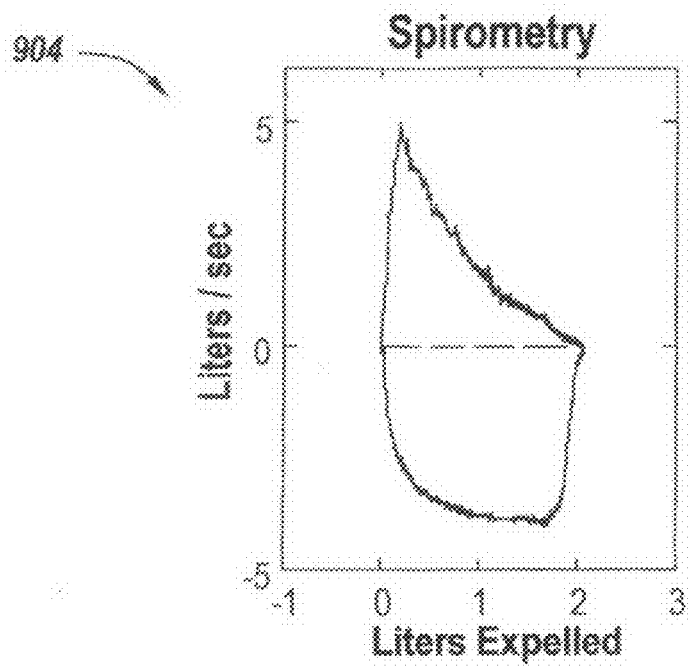
FIG. 8B illustrates an exemplary spirogram representing spirometry data gathered using the airflow measuring device of the present invention.
Figure 8C:
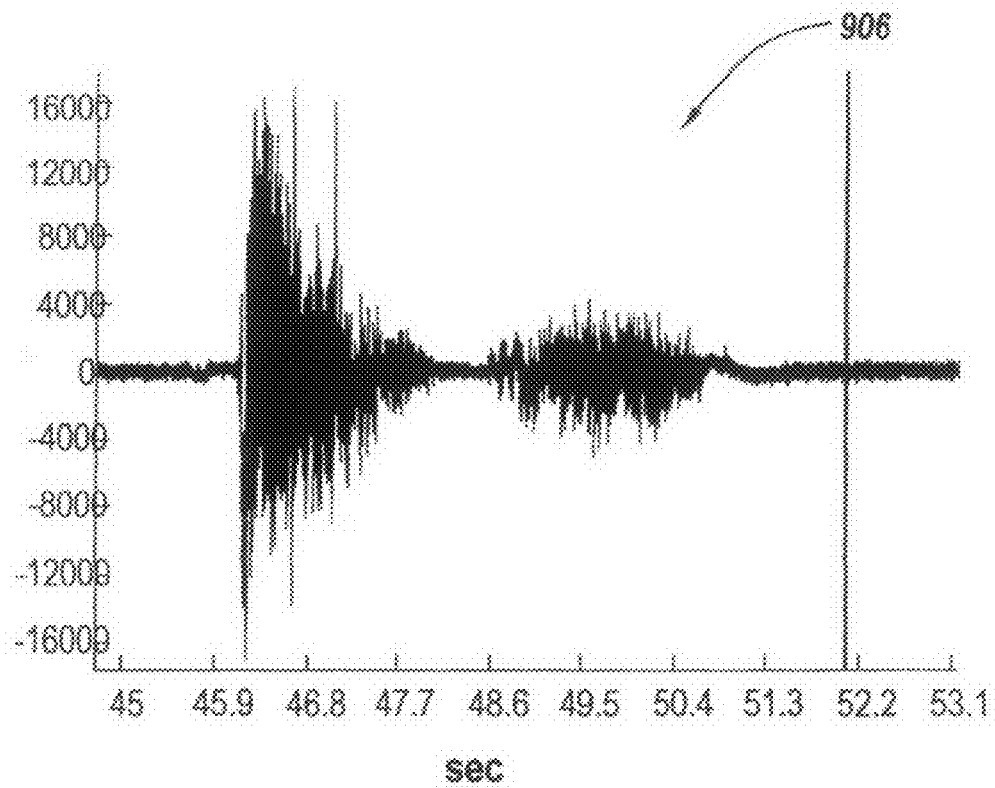
FIG. 8C illustrates expiratory and inspiratory recordings from a sound card according to an exemplary embodiment of the present invention.

The output of the airflow rate determining unit 706 and the sound determining unit 708 (736 and 738 respectively) may be visually represented. FIGS. 8A-8C illustrate various way of visually representing the spirometry data and the sound data detected and/or measured using the airflow measuring device 500 of the present invention. An adult male is used as a subject to collect the data illustrated in FIGS. 8A and 8B. FIG. 8A illustrates the auscultation data and FIG. 8B illustrates the spirometry data, both simultaneously measured using a single airflow sensor.

FIG. 8A illustrates a three dimensional plot 902 of frequency, time and auscultation data of an adult male subject. A Fast Fourier Transform may be performed on the auscultation intensity data. The airflow sensor of the present invention is a bidirectional sensor, i.e. the sensor of the present invention may measure both the inhalation and exhalation data. Accordingly, both the inhalation data 903 and the exhalation data 905 are represented on the three dimensional plot 902 of FIG. 8A.

FIG. 8B illustrates the spirogram 904 of the adult male subject. The data illustrated on FIG. 8B may be collected using the same airflow sensor used to detect the data illustrated on FIG. 8A. It is also possible to record the breath sound data at the output of a sound card. FIG. 8C illustrates expiratory and inspiratory recordings 906 from the sound card.

Figure 9A:
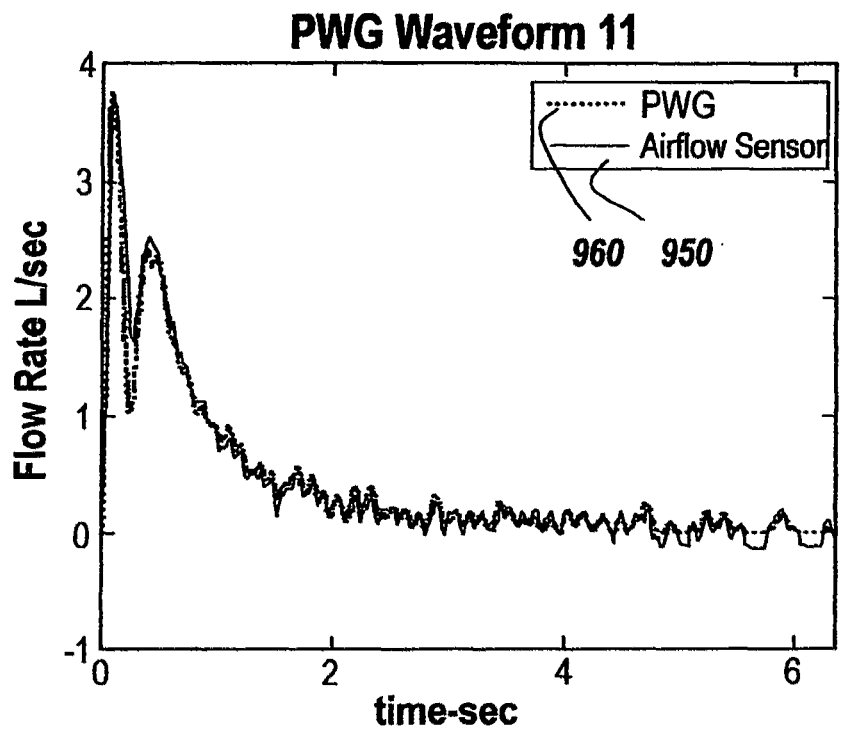
FIGS. 9A-9B is a graphical depiction showing a comparison between data gathered using an airflow sensor according to the teachings of the present invention and simultaneous data gathered using a conventional Pulmonary Waveform Generator (PWG)
Figure 9B:
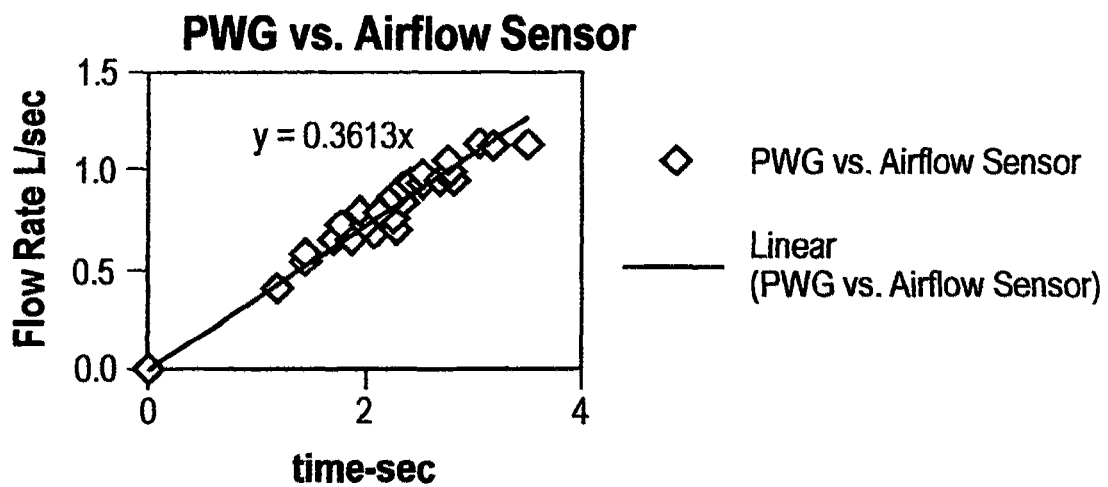

The airflow sensor of the present invention is tested with various applications. The American Thoracic Society publishes spirometry waveforms for the purpose of spirometer calibration and validation of accuracy. These waveforms are fed from a computer into a pulmonary waveform generator (PWG) consisting of a computer-directed servo-controlled pump which generates airflow according to those patterns, which a spirometer can then be tested for its ability to track. FIGS. 9A and 9B compare the standard pulmonary waveform #11 output of a PWG with the recording by the airflow sensor of the present invention. In FIGS. 9A-9B, the data 950 gathered using an exemplary airflow sensor of the present invention are compared to the standard pulmonary waveform #11 data 960 of the PWG.

FIG. 9A illustrates the response of the airflow sensor according to the present invention versus the observed and calibrated PWG curve. The PWG curve is characterized by two initial humps followed by a decay. As illustrated in FIG. 9A, the sensor of the present invention provides data that match well with the output of the PWG.

FIG. 9B shows a comparison of peak expiratory flow $(PEF)^{1/2}$ from the PWG data set versus the maximum voltages obtained from the airflow sensor of the present invention. As illustrated, a linear correlation is observed.

Figure 10:
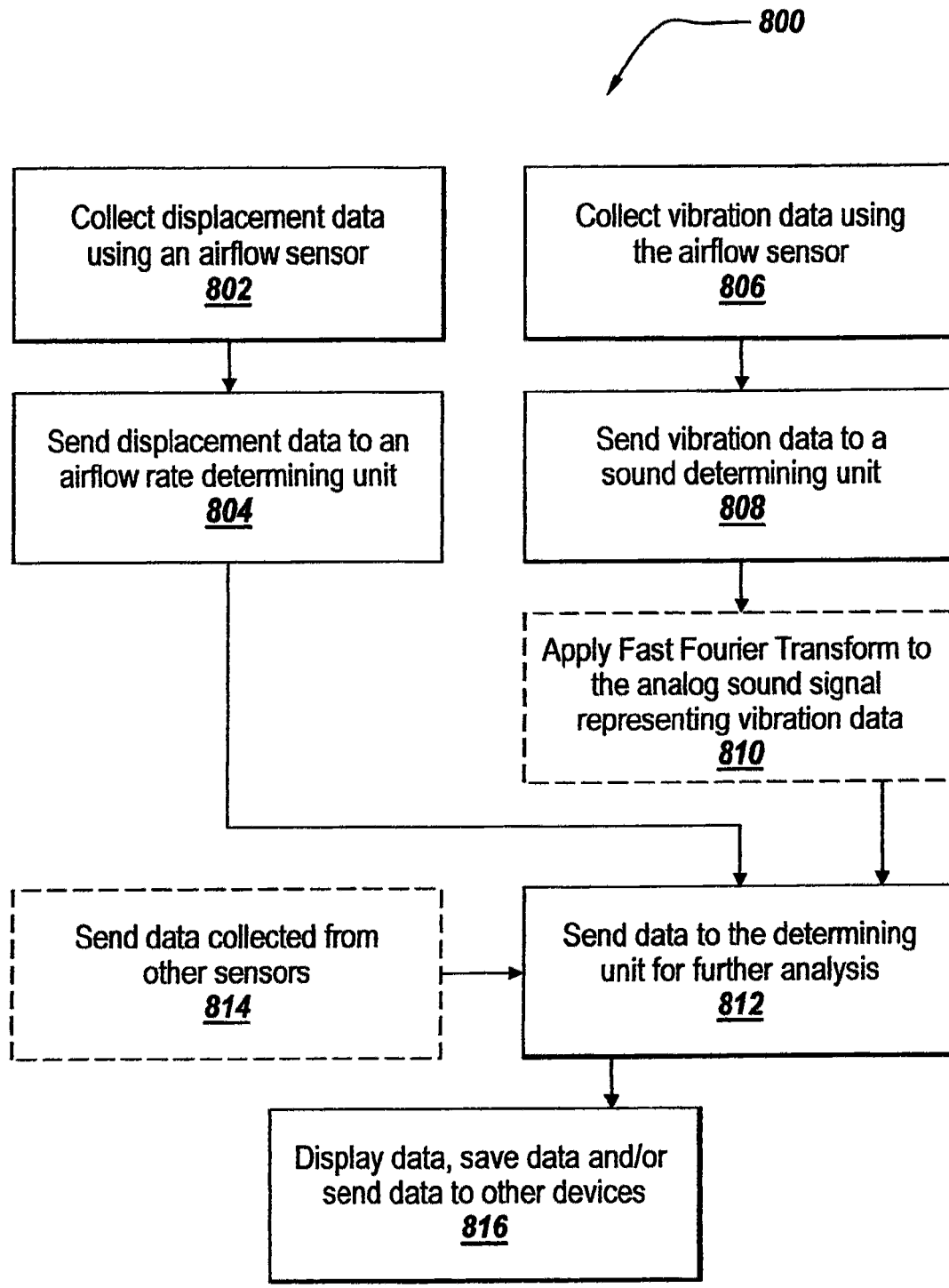
FIG. 10 is a flowchart of steps illustrating an exemplary method of simultaneously gathering spirometry and auscultation data using the airflow sensor of the present invention according to an exemplary embodiment of the present invention.

A flowchart 800 of steps illustrating an exemplary method of simultaneously gathering spirometry and auscultation data using the airflow sensor of the present invention is provided in FIG. 10. The method includes collecting displacement data using a sensor according to the present invention (step 802). The displacement data relates to the displacement of the flap including the sensor caused by the airflow generated by a source. The displacement data may be used to measure the airflow rate of the source, such as a patient. The displacement data may be used as the spirometry data. According to various embodiments of the present invention, the displacement data is sent to an airflow rate determining unit (step 804). The airflow rate determining unit may include an analog-to-digital converter.

The method further includes collecting vibration data using the same sensor of the present invention (step 806). The vibration data relates to the vibration of the flap including the airflow sensor caused by the airflow generated by the source. The vibration data may be used to measure the sound of the source. The vibration data may be used as the auscultation data. The vibration data is sent to a sound processing unit (step 808). The sound processing unit may include a sound card. Accordingly, the method collects two sets of data, i.e. displacement data and vibration data, using the same sensor.

The use of a thin film flexible polymeric in the present invention allows modal vibrations to be used as a mechanism for representing sound. Any physical object subjected to a force that allows slippage, whether it be a flute subjected to airflow slipping across its mouthpiece or a violin with a bow slipping over a string, will have resonance modal vibrations that are activated when the applied force meets specific physical conditions. When specific air velocities are achieved with the elastic flap sensor of the present invention, resonance conditions are satisfied and the timing, frequency and energy of the resulting sonic vibrations can be quantified if the data set is converted by such analytic modalities as Fast Fourier Transform algorithms.

Accordingly, in step 810 of the flowchart 800 of FIG. 10, a Fast Fourier Transform or other algorithms may be applied to the analog sound data signal representing the vibration data in order to decompose the sequence of values collected by the airflow sensor into components of different frequencies for further analysis (step 810). The result of the Fast Fourier Transform and/or the raw data collected by the airflow sensor is sent to a determining unit for further analysis (step 812) and visual representation (step 816). If additional data are collected by other sensors (step 814), such as chemical sensors or thermal sensors, used in conjunction with the airflow sensor of the present invention, the additional data may also be sent to the determining unit to be analyzed along with the displacement and vibration data (step 812). When the collected data are analyzed using the determining unit, the data may be visually displayed, saved, or sent to other devices (step 816).

The present invention provides a new class of airflow sensors, in which the indicator of airflow is the elastic deformation of a flexible flap. The flexible flap does not require additional appendages for controlling vibration. The elimination of additional appendages prevents trapping of respiratory secretions and results in a device that is easy to clean and disinfect. The primary intended use of the airflow sensor according to the present invention is medical measurement of human respiratory airflow and breathing sounds for diagnostic and therapeutic purposes. However, the primary intended use should not be construed as limiting. Multiple embodiments are envisioned in which the flap can accommodate a plurality of other physical and chemical sensors.

The present invention is not limited to medical applications. An exemplary non-medical use of the present invention may be the measurement of airflow across the various surfaces of aircraft in flight. The airflow sensors of the present invention may be used to measure airflow with the particular advantage that the elastic flap devices of the present invention are very sensitive under stall conditions. Unlike pitot tubes, flaps built into the wings and bodies of commercial jet aircraft do not plug up with ice.

Another exemplary non-medical implementation of the present invention is a device mounted at the top of a mast of a sailboat that measures the wind speed, direction, and sound. The device may have a strain gauge in a tube. As wind goes through the tube, the sensor is bent, giving a change in resistance. The gauge may be connected to a cable capable of 360 degree rotation. A Wheatstone bridge may be used to monitor the change in resistance. The measurements of the strain gauge may be conveyed to a computing device. Using the sound card of the computing device, the user may hear low frequency sound indicative of adverse sail flapping, which could tell the user that a stall condition has occurred.

Other potential non-medical applications include monitoring air flow and vibrations in acoustical wind instruments from pipe organs to saxophones. Both medical and industrial embodiments of the airflow sensor can be modular, allowing cleaning and disinfection of the sensor.

While the invention has been shown and described with reference to specific preferred embodiments, it should be understood by those skilled in the art that various changes in form and detail may be made therein without departing from the spirit and scope of the invention as defined by the following claims.

What is claimed is:

1. A fluid flow sensing system for measuring a fluid flow, said fluid flow sensing system comprising:
    a housing having a chamber that is sized and dimensioned to allow the fluid to pass therethrough;
    a flap coupled to said chamber, wherein the fluid causes said flap to move when the fluid passes thereover;
    a plurality of piezoresistive sensors including a first sensor disposed on a first side of said flap and a second sensor disposed on a second side of said flap, said first and second sensors being identical and symmetric with respect to at least one axis of symmetry, said first and second sensors each having a first circuit portion and a second circuit portion, said first circuit portions of said first and second sensors configured to sense a change in a first resistance of said first and second sensors in response to a displacement of said flap, said second circuit portions of said first and second sensors configured to sense a change in a second resistance of said first and second sensors in response to a vibration of said flap, said first and second sensors generating a plurality of sensor output signals, said plurality of sensor output signals containing a first sensor signal component generated by said first circuit portions and representative of said displacement of said flap, said plurality of sensor output signals containing a second sensor signal component generated by said second circuit portions and representative of said vibration of said flap, said displacement of said flap being representative of a flow rate of the fluid and said vibration of said flap being representative of a frequency characteristic associated with the fluid;
    a digital signal processor, said digital signal processor including a determining unit including a processor and a memory, said determining unit having a fluid flow rate determining unit and a sound determining unit, said digital signal processor and said determining unit coupled to said first and second sensors and receiving said plurality of sensor output signals, said determining unit having a voltage conversion unit for transducing said first sensor signal component and said second sensor signal component into a first transduced sensor signal component and a second transduced sensor signal component respectively, said determining unit including an amplification unit for amplifying said first and second transduced sensor signal components, said first and second transduced and amplified sensor signal components presented to said fluid flow rate determining unit and said sound determining unit respectively, said fluid flow rate determining unit generating a fluid flow rate signal representative of said flow rate of the fluid from said first transduced and amplified sensor signal component, said sound determining unit generating sound signals representative of said frequency characteristic associated with the fluid from said second transduced and amplified sensor signal component; and
    a computing device having a processor and a memory, said computing device receiving said fluid flow rate signal and said sound signals, said computing device determining said flow rate of the fluid using said fluid flow rate signal, and said computing device determining said frequency characteristic using said sound signals.

2. The system of claim 1 wherein said computing device is coupled to a display device, said fluid flow is a respiratory air flow from a subject's mouth, said fluid flow sensing system generating said fluid flow rate signal including data representative of the subject's air flow rate, said fluid flow sensing system generating said sound signals including data representative of the subject's breath sound characteristics, said computing device presenting said data representative of the subject's air flow rate and said data representative of the subject's breath sound characteristics to said display device, said display device presenting said data representative of the subject's airflow rate as a spirometry flow-volume loop, said display device presenting said data representative of the subject's breath sound characteristic as a frequency waveform.

3. The system of claim 2 wherein said fluid flow sensing system is one of a Forced Oscillation Technique (FOT) device or an Impulse Oscillometry (IOS) device.

4. The system of claim 1 wherein said flap is made of a polyimide film.

5. The system of claim 1 wherein said first circuit portions and said second circuit portions each comprise parallel piezoresistive sensor strips and said first and second circuit portion of each sensor are perpendicular to each other.

6. The system of claim 1 wherein said flap is composed of a material having a Young's modulus in a range of about 0.1 to 7.0 GPa.

7. The system of claim 1 wherein said fluid flow rate determining unit further comprises:
an analog-to-digital converter for converting said first transduced and amplified sensor signal component into a digital sensor output signal; and
a calculation unit for generating said fluid flow rate signal based upon said digital sensor output signal.

8. The system of claim 7 wherein said calculation unit includes calibration data used by said calculation unit to correlate said digital sensor output signal to a predetermined calibration curve.

9. The system of claim 1 wherein said sound determining unit comprises:
a sound processing unit for generating said sound signals in response to said second transduced and amplified sensor signal component, and;
a frequency conversion unit for receiving said sound signals and in response thereto converting said sound signals into a frequency signal.

10. The system of claim 9 wherein said sound processing unit includes a sound card.

11. The system of claim 9 wherein said frequency conversion unit includes a fast Fourier transform module.

12. The system of claim 1 wherein said fluid flow sensing system measures an airway impedance; said computing device using said plurality of piezoresistive sensors to determine said airway impedance.

13. The system of claim 1 wherein said voltage conversion unit is a Wheatstone bridge.

14. A method for determining both a flow rate and a frequency characteristic of a fluid with a fluid flow sensing system, said fluid flow sensing system having a housing and a chamber that is sized and dimensioned to allow said fluid to pass therethrough, said fluid flow sensing system having a moveable flap coupled to said chamber, said moveable flap having a plurality of piezoresistive sensors including a first sensor disposed on a first side of said flap and a second sensor disposed on a second side of said flap said first sensor and said second sensor each having a first circuit portion and a second circuit portion, said first circuit portions configured to sense a change in a first resistance of said sensors in response to a displacement of said flap, said displacement of said flap being representative of a flow rate of the fluid, said second circuit portions configured to sense a change in a second resistance of said sensors in response to a vibration of said flap, said vibration of said movable flap being representative of a frequency characteristic associated with the fluid, said method comprising:
inputting the fluid into said fluid flow sensing system, said moveable flap deflecting and vibrating in response to said input fluid;
generating a plurality of sensor output signals from said plurality of piezoresistive sensors in response to said deflection and vibration of said flap, said step of generating including:
generating a plurality of first sensor signal components with said first circuit portions when said first resistance of said sensors changes; and
generating a plurality of second sensor signal components with said second circuit portions when said second resistance of said sensors changes;
receiving said plurality of sensor output signals; including said plurality of first sensor signal components and said plurality of second sensor signal components, at a determining unit, said determining unit including a processor and a memory, a voltage conversion unit, an amplification unit, a fluid flow rate determining unit and a sound determining unit;
transducing said plurality of first and said plurality of second sensor signal components with said voltage conversion unit;
amplifying said transduced first and said transduced second sensor signal components with said amplification unit;
generating with said fluid flow rate determining unit a fluid flow rate signal from said plurality of transduced and amplified first sensor signal components of said sensor output signals, said fluid flow rate signal representative of said flow rate of the fluid;
determining with a computing device said flow rate of the fluid using said fluid flow rate signal, said computing device having a processor and a memory, said computing device coupled to said determining unit;
generating with said sound determining unit sound signals from said plurality of transduced and amplified second sensor signal components of said sensor output signals, said sound signals representative of said frequency characteristic associated with the fluid; and
determining with said computing device said frequency characteristic of the fluid using said sound signals.

15. The method of claim 14 wherein said steps of generating said plurality of first and said plurality of second signal components occur simultaneously using said plurality of piezoresistive sensors.

16. The method of claim 14 wherein said step of generating with said sound determining unit sound signals further comprises:
generating an audible sound with a sound card, said sound card coupled to said sound determining unit, said audible sound representative of a sound associated with the fluid.

17. The method of claim 16 wherein said step of generating with said sound determining unit sound signals further comprises the steps of:
generating a frequency data signal based on said plurality of transduced and amplified second sensor signal components of said sensor output signals; and
converting said frequency data signal into a frequency waveform.

18. The method of claim 16 wherein the fluid is a respiratory air flow from a subject's mouth, and said frequency characteristic is an auscultation measurement, said audible sound representing a sound characteristic of said respiratory air flow.

19. The method of claim 14 wherein said fluid flow sensing system and said computing device are coupled to a display device, said fluid flow is a respiratory air flow from a subject's mouth, said method further comprising:
generating data representative of the subject's airflow rate as part of the step of generating said fluid flow rate signal;
displaying on said display device, using said computing device said data representative of the subject's airflow as a spirometry flow-volume loop;
generating data representative of the subject's breath sound characteristics as part of the step of generating said sound signals; and displaying on said display device, using said computing device, said data representative of the subject's breath sound characteristics as a frequency waveform.

\* \* \* \* \*